(12) United States Patent
Lim et al.

(10) Patent No.: US 11,712,490 B2
(45) Date of Patent: Aug. 1, 2023

(54) STERILIZATION APPARATUS

(71) Applicant: PLASMAPP CO., LTD., Daejeon (KR)

(72) Inventors: Youbong Lim, Daejeon (KR); Seunghun Lee, Seoul (KR); Junyoung Kim, Daejeon (KR); Miseon Hwang, Daejeon (KR)

(73) Assignee: PLASMAPP CO., LTD., Daejeon (KR)

( * ) Notice: Subject to any disclaimer, the term of this patent is extended or adjusted under 35 U.S.C. 154(b) by 628 days.

(21) Appl. No.: 16/607,954

(22) PCT Filed: Mar. 6, 2018

(86) PCT No.: PCT/KR2018/002650
§ 371 (c)(1),
(2) Date: Oct. 24, 2019

(87) PCT Pub. No.: WO2018/199462
PCT Pub. Date: Nov. 1, 2018

(65) Prior Publication Data
US 2020/0138994 A1  May 7, 2020

(30) Foreign Application Priority Data

Apr. 25, 2017 (KR) .......................... 10-2017-0052738

(51) Int. Cl.
*A61L 2/20* (2006.01)
*A61L 2/26* (2006.01)

(52) U.S. Cl.
CPC ................ *A61L 2/208* (2013.01); *A61L 2/26* (2013.01); *A61L 2202/11* (2013.01);
(Continued)

(58) Field of Classification Search
CPC ........ A61L 2/208; A61L 2/26; A61L 2202/11; A61L 2202/121; A61L 2202/122;
(Continued)

(56) References Cited

U.S. PATENT DOCUMENTS 5,882,416 A * 3/1999 Van Buskirk ......... C23C 16/448
261/106
6,364,604 B1 * 4/2002 Nonaka ............... F04D 25/0613
415/111
(Continued)

FOREIGN PATENT DOCUMENTS

KR  2001-0104380 A  11/2001
KR  2002-0077887 A  10/2002
(Continued)

OTHER PUBLICATIONS

International Search Report for PCT/KR2018/002650 dated Aug. 20, 2018 (PCT/ISA/210).
(Continued)

*Primary Examiner* — Regina M Yoo
(74) *Attorney, Agent, or Firm* — Sughrue Mion, PLLC

(57) ABSTRACT

The present invention provides a sterilization apparatus. The sterilization apparatus comprises a sterilant extractor configured to extract a sterilant using an auxiliary needle from a sterilant cartridge disposed inside or outside a sterilization chamber and a sterilant supplier configured to receive the sterilant extracted through the auxiliary needle, to vaporize the sterilant through a vaporizer, and to provide the vaporized sterilant to the sterilization chamber or a vacuum pouch disposed inside the sterilization chamber through a main needle.

13 Claims, 12 Drawing Sheets

(52) U.S. Cl.
    CPC ... *A61L 2202/121* (2013.01); *A61L 2202/122* (2013.01); *A61L 2202/123* (2013.01); *A61L 2202/15* (2013.01)

(58) Field of Classification Search
    CPC ........... A61L 2202/123; A61L 2202/15; A61L 2202/181; A61L 2202/24; A61L 2/20; A61L 2202/14
    See application file for complete search history.

(56) References Cited

U.S. PATENT DOCUMENTS

| | | | |
|---|---|---|---|
| 6,495,100 | B1 | 12/2002 | Lin et al. |
| 7,854,962 | B2 * | 12/2010 | Kasai ................. C23C 16/4481 427/255.28 |
| 2006/0280646 | A1 | 12/2006 | Shiosawa |

FOREIGN PATENT DOCUMENTS

| | | |
|---|---|---|
| KR | 10-2007-0006694 A | 1/2007 |
| KR | 10-1224842 B1 | 1/2013 |
| KR | 10-1273764 B1 | 6/2013 |
| KR | 10-2017-0017023 A | 2/2017 |

OTHER PUBLICATIONS

Korean Notification of Reason for Refusal for 10-2017-0052738 dated, Nov. 2, 2018.

* cited by examiner

STERILIZATION APPARATUS

TECHNICAL FIELD

The present disclosure relates to a sterilization apparatus for providing a certain amount of sterilant to a sterilization space through a vaporizer, and more particularly, to a sterilization apparatus for stably supplying a small amount of sterilant.

BACKGROUND ART

A sterilizer is a chemical sterilizer which performs a sterilization process by vaporizing a liquid sterilant such as a hydrogen peroxide ($H_2O_2$) solution and supplying the vaporized sterilant to a sterilization chamber.

In a sterilizer using hydrogen peroxide as a sterilant, the sterilization chamber is formed with a base vacuum of 10 Torr or less, a vaporizer vaporizes the sterilant and injects the sterilant into the sterilization chamber, the vaporized sterilant is diffused in the sterilization chamber, and the vaporized sterilant performs a sterilization process on an exposed article to be sterilized.

In such a vacuum state, vaporization may occur at a relatively low temperature (e.g., 100° C. or less), and the amount of injected sterilant may be defined so that the injected sterilant may exist in a gaseous state even at the pressure of the diffusing process.

As such, the sterilant needs to be maintained in the gaseous state to be delivered to and within the article to be sterilized in the sterilization chamber and to perform the sterilization process stably.

A conventional sterilizer generally has a sterilization chamber of tens of liters or more, and the supply amount of sterilant is at a level of several milliliters in an environment of about 55° C. When a sterilant above saturated vapor pressure is injected, partial condensation occurs inside the sterilization chamber. In addition, the sterilant is difficult to deliver sufficiently to the article to be sterilized and it is difficult to expect reliable sterilization. Also, condensation of a highly oxidizing sterilant such as hydrogen peroxide inside or on the surface of the article to be sterilized, if the sterilant remains in the article to be sterilized even after the process, may result in exposure to a user, which makes it difficult to ensure the safety of the sterilization process. Meanwhile, if a sufficient amount of sterilant is not injected, concentration of the sterilant in the sterilization chamber is low and sterilization efficiency is low, and successful sterilization is difficult to achieve. As such, the supply of a proper amount of sterilant suitable for the sterilization environment is required to ensure the reliability and safety of the sterilization process.

In a conventional sterilizer, a sterilant supply may be implemented using a commercially available solenoid valve. When such a solenoid valve is used, the cross section of a pipe through which hydrogen peroxide is delivered cannot always be kept constant by an internal structure and a connector. In addition, hydrogen peroxide accumulates in the valve and in the connector, or hydrogen peroxide remaining in the previous process is delivered together in the next process, so that it is difficult to supply a certain amount of sterilant. In particular, it is very difficult to ensure sterilization reliability in delivering a small amount of hydrogen peroxide. In addition, a strong acidic sterilant may cause malfunction of the valve by reacting with an internal structure of the valve and has a problem that it is difficult to secure reliability for long-term use.

DESCRIPTION OF EMBODIMENTS

Technical Problem

The present disclosure is directed to a sterilant supply to prevent loss of a sterilant during the supply of the sterilant from a sterilant cartridge.

The present disclosure is directed to a sterilant supply for ensuring the safety of a user in mounting a sterilant cartridge.

The present disclosure is directed to a sterilant cartridge that stores an appropriate amount of sterilant and supplies the sterilant to a sterilization space.

The present disclosure is not limited to the above objectives, but other objectives not described herein may be clearly understood by those of ordinary skill in the art from descriptions below.

Solution to Problem

According to an aspect of the present disclosure, a sterilization apparatus comprises a sterilant extractor configured to extract a sterilant using an auxiliary needle from a sterilant cartridge disposed inside or outside a sterilization chamber; and a sterilant supplier configured to receive the sterilant extracted through the auxiliary needle, to vaporize the sterilant through a vaporizer, and to provide the vaporized sterilant to the sterilization chamber or a vacuum pouch disposed inside the sterilization chamber through a main needle.

According to an example embodiment, the sterilization apparatus further comprises a sterilant supply valve between the auxiliary needle and the sterilant supplier to adjust the sterilant extracted from the sterilant cartridge to be supplied to the sterilant supplier.

According to an example embodiment, the sterilant supply valve comprises an elastic pipe of elastic material between the auxiliary needle and the vaporizer; and a compressor pressing and closing the elastic pipe.

According to an example embodiment, the compressor comprises a pressing head configured to press the elastic pipe locally; an elastic spring disposed to surround a lower side surface of the pressing head; a pressing head pipe disposed to surround an upper side surface of the pressing head; and a pressing head receiver recessed locally to receive the pressing head and fixed to the vaporizer.

According to an example embodiment, the sterilization apparatus further comprises a sterilant supply pipe configured to connect the vaporizer to the elastic pipe, wherein one end of the sterilant supply pipe is connected to the vaporizer, the other end of the sterilant supply pipe is bent to extend in a direction perpendicular to a moving direction of the pressing head, and the elastic pipe is bent into an "L" shape.

According to an example embodiment, the sterilization apparatus further comprises an auxiliary needle transfer portion configured to linearly move the sterilant extractor so that the auxiliary needle punctures the sterilant cartridge, which is disposed in the sterilization chamber, to extract the sterilant; and a main needle transfer portion configured to linearly move the sterilant supplier so that the main needle communicates with a sterilant injection path disposed in the sterilant cartridge.

According to an example embodiment, the auxiliary needle transfer portion comprises an auxiliary needle supporter configured to support the auxiliary needle; an auxiliary needle transfering body configured to fix the auxiliary needle supporter and the compressor; an auxiliary needle slide fixedly coupled to the auxiliary needle transfering body and performing linear motion; an auxiliary needle linear motion guide configured to guide the auxiliary needle slide; a rack gear configured to provide a driving force to the auxiliary needle transfering body; a pinion gear in gear engagement with the rack gear; and a motor configured to rotate a central axis of the pinion gear.

According to an example embodiment, the main needle transfer portion comprises a main needle slide fixedly coupled to the vaporizer and performing linear motion; a main needle linear motion guide configured to guide the main needle slide; a rack gear configured to provide driving force to the vaporizer; a pinion gear in gear engagement with the rack gear; and a motor configured to rotate a central axis of the pinion gear.

According to an example embodiment, the vaporizer comprises a cylindrical vaporizer body tube comprising a first connection port connected to the main needle and a second connection port connected to a vacuum pump; a heater disposed to surround an evaporation body tube; a main pipe inserted into the vaporizer body tube; a conductance adjuster between the vaporizer body tube and the main pipe; and a sterilant supply pipe connected to a lower side of the vaporizer body tube, wherein a sterilant supplied through the sterilant supply pipe is evaporated between the vaporizer body tube and the main pipe to move along the conductance adjuster and is discharged to an inner upper portion of the vaporizer body tube.

According to an example embodiment, the vaporizer comprises a heat reflection tube disposed to surround the heater; and an insulator between the heater and the heat reflection tube.

According to an aspect of the present disclosure, An operating method of a sterilization apparatus comprising: a sterilant extractor configured to extract a sterilant using an auxiliary needle from a sterilant cartridge disposed inside or outside a sterilization chamber; and a sterilant supplier configured to receive the sterilant extracted through the auxiliary needle, to vaporize the sterilant through a vaporizer, and to provide the vaporized sterilant to the sterilization chamber or a vacuum pouch disposed inside the sterilization chamber through a main needle, the operating method comprises vacuum evacuating the sterilization chamber or the vacuum pouch disposed inside the sterilization chamber using the main needle while a connection path between the vaporizer and the auxiliary needle is closed; extracting the sterilant contained in the sterilant cartridge using the auxiliary needle while the connection path between the vaporizer and the auxiliary needle is opened, and injecting the sterilant into the sterilization chamber or the vacuum pouch through the vaporizer; sterilizing a target object in the sterilization chamber or the vacuum pouch while the connection path between the vaporizer and the auxiliary needle is closed; and exhausting the sterilant diffused in the sterilization chamber or the vacuum pouch.

According to an example embodiment, the operating method further comprises venting the sterilization chamber or the vacuum pouch by injecting external air into the sterilization chamber or the vacuum pouch.

According to an example embodiment, an open/close state of the connection path between the vaporizer and the auxiliary needle is determined by positions of the auxiliary needle and the main needle, the open/close state of the connection path is achieved by compression of the elastic pipe, and the open state of the connection path is achieved when both the auxiliary needle and the main needle are raised to penetrate the sterilant cartridge.

Advantageous Effects of Disclosure

A sterilization apparatus according to an embodiment of the present disclosure may ensure reliability of a sterilization process by supplying a certain amount of sterilant while ensuring user safety.

MODE OF DISCLOSURE

Figure 1:
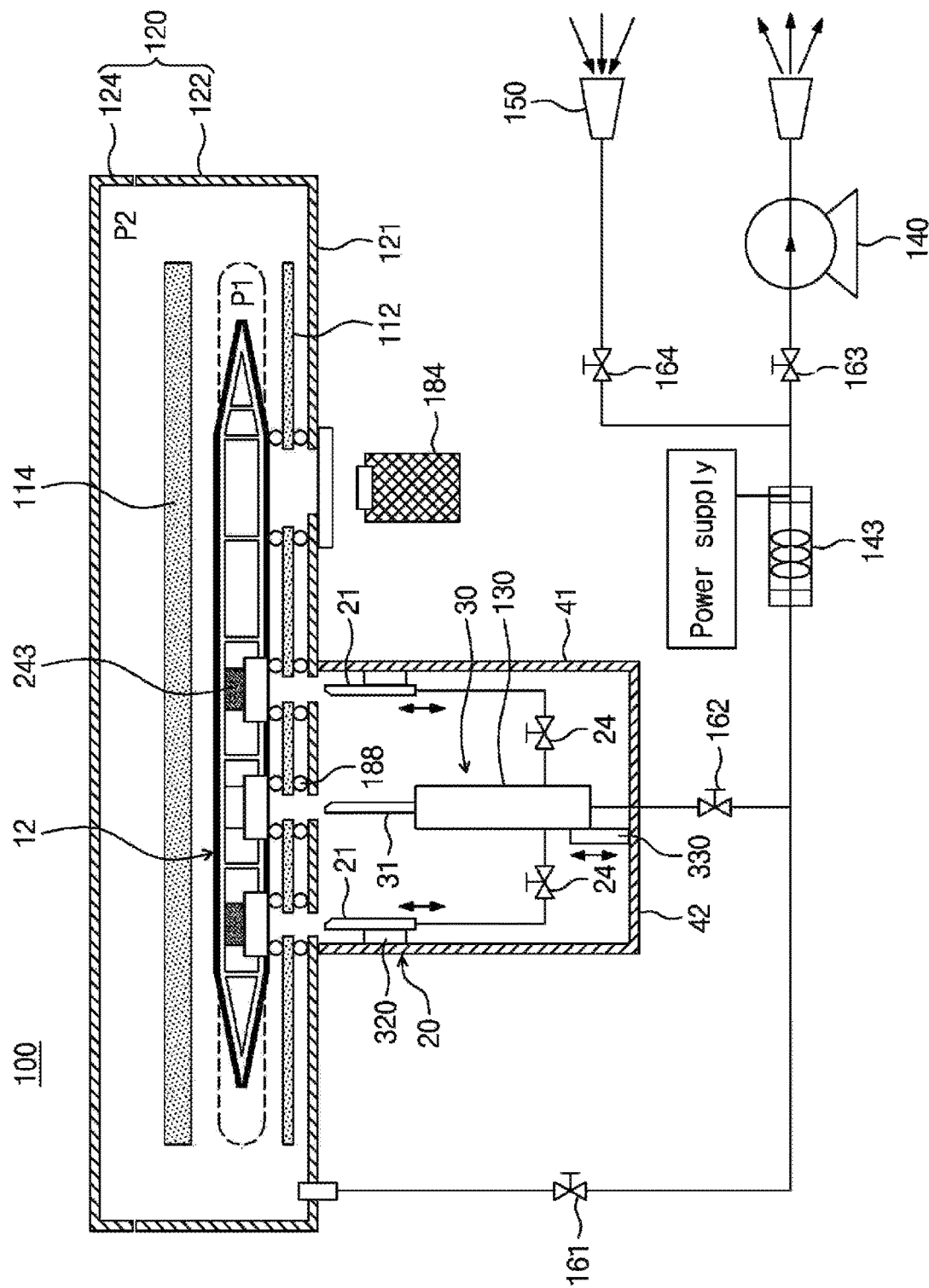
FIGS. 1 to 3 are conceptual diagrams of a sterilization apparatus according to an embodiment of the present disclosure.

As the size of a sterilization chamber of a sterilizer decreases, a small amount of hydrogen peroxide to be injected is used, and thus a technique for precisely controlling a small amount of hydrogen peroxide is required. In order to supply a fixed amount of hydrogen peroxide to the sterilization chamber or a sterilization space, hydrogen peroxide extracted from a sterilant cartridge needs to be delivered to a vaporizer without being lost or accumulated in a sterilant supply path. In addition, repeatable reliability of a sterilization process needs to be ensured.

According to an embodiment of the present disclosure, an auxiliary needle is used to deliver a sterilant from a sterilant cartridge with at least one sterilant cell to a vaporizer.

According to an embodiment of the present disclosure, a valve between the sterilant cartridge and the vaporizer includes an elastic tube and a compressor that physically deforms the elastic tube to open and close the tube. The elastic tube may operate as a sterilant supply line in a non-deformed state, and the elastic tube may operate as a valve to prevent movement of the sterilant in the deformed state.

The elastic tube and the compressor for opening and closing the elastic tube may form a vacuum boundary of the sterilization chamber. In addition, the elastic tube and the compressor for opening and closing the elastic tube may operate as a sterilant supply to prevent loss of the sterilant.

According to an embodiment of the present disclosure, the elastic tube has a constant cross section and may constitute a pipe of the shortest distance between the auxiliary needle and the vaporizer. A structure for pressing the elastic tube may not constitute a conventional valve to solve the problem of loss of a sterilant or accumulation of a sterilant in a pipe and may provide a sterilization process with repeatable reliability.

According to an embodiment of the present disclosure, an auxiliary needle is connected to a driver and remains in a retracted state except for a sterilant extraction operation. Accordingly, in mounting a sterilant cartridge and removing the sterilant cartridge after use, the auxiliary needle may be set not to be directly exposed to a user, thereby ensuring user safety.

According to an embodiment of the present disclosure, an appropriate amount of sterilant is contained in a sterilant cartridge mounted on a packaging container, and the sterilant contained in the sterilant cartridge is sealed using an elastic body such as silicone. Therefore, when the auxiliary needle penetrates the elastic body and extracts the sterilant, the sterilant does not leak. Accordingly, user safety and reliability of a sterilization process may be ensured.

Typically, a sterilization chamber has a vacuum pumping line to maintain vacuum, a sterilant injection line for vaporizing and injecting a sterilant, and a separate venting line for injecting external air.

Multiple pipelines occupy a large space, reducing space utilization and increasing costs. In particular, a structure of multiple pipelines is not suitable when a volume-variable target object storage container (or vacuum pouch) is provided in the sterilization chamber. In more detail, a sterilization apparatus according to an embodiment of the present disclosure includes a fixed volume sterilization chamber and a volume-variable target object storage container (or vacuum pouch) that varies according to a pressure difference. The volume-variable target object storage container may include a vacuum pouch. It is not easy to independently connect a vacuum pumping line, a sterilant injection line, and a venting line to the vacuum pouch. The vacuum pumping line, the sterilant injection line, and the venting line need to be integrated into one.

Therefore, an embodiment of the present disclosure provides a new vaporizer that acts as a vaporizer for treating a plurality of such pipelines in one line while vaporizing a sterilant. The volume-variable target object storage container may be a plastic film vacuum pouch. The volume of the volume-variable target object storage container may be varied by a pressure difference between the sterilization chamber and the volume-variable target object storage container.

In addition, the volume-variable target object storage container includes a sterilant cartridge of a solid shape, and vacuum sealing is performed between the sterilant cartridge and the sterilization chamber. Accordingly, a portion of a sterilant injection path stopper of the sterilant cartridge is exposed to the atmosphere through an opening of the chamber. The vaporizer has a main needle. When a sterilant is injected into the volume-variable target object storage container or the volume-variable target object storage container is vacuum evacuated, the main needle performs an exhaust or sterilant injection process by puncturing the sterilant injection path stopper.

A vaporizer according to an embodiment of the present disclosure may provide a structure that may be implemented as a single component that integrates a vacuum pumping line, a venting line, and a sterilant injection line. The vaporizer includes a vaporizer body tube, a heater arranged to surround the evaporator body tube, and a main pipe inserted into the vaporizer body tube. The main pipe may operate as a venting line and a vacuum pumping line. A space between the vaporizer body tube and the main pipe may act as a sterilant injection line. The vaporizer body tube is cylindrical in shape and includes a first connection port connected to a volume-variable target object storage container in a sterilization chamber and a second connection port connected to a vacuum pump. The space between the vaporizer body tube and the main pipe is a double tube structure and may have conductance sufficiently less than conductance of the main pipe. Even when the main pipe is connected to the vacuum pump, the space between the vaporizer body tube and the main pipe may provide sufficiently low pressure to the volume-variable target object storage container. Meanwhile, when the second connection port is closed through a valve and a liquid sterilant is injected into the space between the vaporizer body tube and the main pipe, the volume-variable target object storage container may be filled with a vaporized sterilant.

The space between the vaporizer body tube and the main pipe may be heated by a heater, and an orifice or thread may be used to increase fluid resistance and to secure a residence time of a sterilant to be injected. The orifice or thread sprays a sterilant at a relatively high flow rate, so that the vaporized sterilant may be delivered at a higher probability to the volume-variable target object storage container.

A vaporizer according to an embodiment of the present disclosure is a tube structure connected between a volume-variable target object storage container and a vacuum pump to ensure conductance for sufficient fluid flow and provide fast vacuum treatment. Using a double tube structure, both functions may be performed simultaneously without the use of separate tubes for vacuum treatment and sterilant injection. In addition, as well as the sterilant injection, venting may be performed through a double tube after the completion of the process. A sterilant to be injected may be supplied towards an inner wall of a vaporizer body tube heated to a high temperature and effectively heated. The sterilant may be secondarily heated through a narrow double tube space while proceeding to an upper relatively low pressure region. Through the orifice or thread, the sterilant is reflected in a blocked area to form a vortex and induce sufficient heating.

Chemical sterilization using a sterilant typically places a pouch inside a sterilization chamber, including a selective permeable film, such as TIVEK, through which the sterilant may permeate a target object. When the sterilant is injected into the sterilization chamber, the sterilant permeates the pouch to sterilize the target object in the pouch. Sterilization efficiency of the sterilization method is drastically reduced due to the separate pouch. In addition, the pouch requires an additional long period of purification to remove the sterilant adsorbed on the pouch in the sterilization process. As the sterilant is injected into the sterilization chamber, a large amount of sterilant is used. The sterilant may cause environmental pollution. Further, the sterilant is usually subjected to an exhaust purification process before being exhausted to the outside. This exhaust purification process deteriorates the performance of a vacuum pump. Therefore, a new sterilization method using a small amount of sterilant is required.

According to an embodiment of the present disclosure, a vacuum pouch is used instead of a sterilization chamber to perform a sterilization process. After completion of the sterilization process, the vacuum pouch may be immediately transferred by a user or stored for a long time. When the sterilant is injected into the vacuum pouch, the volume defined by the vacuum pouch is significantly less than the volume of the conventional sterilization chamber. Therefore, the sterilant usage may be significantly reduced.

According to an embodiment of the present disclosure, the vacuum pouch may be vacuum evacuated under atmospheric pressure by a vacuum pump, and a sterilant may be injected into the vacuum pouch. When the vacuum pouch is in an atmospheric pressure environment, the vacuum pouch shrinks due to a pressure difference between the inside and the outside, and it is difficult to ensure a diffusion space of the sterilant. In order to provide the diffusion space of the sterilant, the vacuum pouch may be arranged in a sterilization chamber maintained at pressure lower than pressure of the vacuum pouch. Accordingly, the vacuum pouch expands due to a low external pressure, thereby securing the diffusion space of the sterilant. Thus, the secured space may provide a path through which the sterilant may diffuse, thereby stably sterilizing a target object such as a lumen. The sterilization chamber is for controlling the external pressure of the vacuum pouch, and the sterilant is not exposed to an inner wall of the sterilization chamber. Accordingly, the air exhausted from the sterilization chamber may be separately purified and may not be exhausted. Therefore, only the sterilant injected into the vacuum pouch may be selectively purified and exhausted.

According to an embodiment of the present disclosure, a sterilant is directly injected into a vacuum pouch capable of vacuum sealing using an impermeable film, and sterilization efficiency is improved by a limited diffusion space of the sterilant. Also, a user safety problem that occurs when the sterilant is absorbed by the vacuum pouch or remains on an outer surface of the vacuum pouch may be solved. In addition, the vacuum pouch may be vacuum packed to provide long-term storage in a sterilized state. The vacuum pouch may maintain the sterilized state even in a contaminated environment, a high temperature environment, and a high humidity environment. A sterilant inlet (or a sterilant cartridge) of the vacuum pouch may be sealed by elasticity of an elastic body such as silicone rubber. The elastic body may provide vacuum evacuation to the outside or sterilant injection into the interior by a needle.

According to an embodiment of the present disclosure, the volume of a vacuum pouch is secured by using a sterilization chamber outside the vacuum pouch without forming a pathway such as an embossing pattern to provide a diffusion space of a sterilant.

According to an embodiment of the present disclosure, it is necessary to ensure the volume of a vacuum pouch for effective diffusion of a sterilant inside the vacuum pouch and supply of the sterilant to an article to be sterilized after direct sterilant supply to the vacuum pouch. For this purpose, an effective sterilization process is enabled by using a sterilization chamber outside the vacuum pouch.

According to an embodiment of the present disclosure, the vacuum pouch is coupled with the sterilant cartridge to provide a sealed internal space. The sterilant cartridge may include a sterilant injection path through which a sterilant may be injected from the outside, and a sterilant container for containing the sterilant. The vacuum pouch may be formed of a polyethylene (PE) film. The vacuum pouch is sealed in a state in which a target object is contained, and vacuum treatment of the vacuum pouch and direct sterilant supply are possible through the sterilant cartridge mounted in the vacuum pouch.

According to an embodiment of the present disclosure, the vacuum pouch is provided with the sterilant cartridge. The sterilant cartridge includes a sterilant container for containing a sterilant, wherein an auxiliary needle may extract the sterilant from the sterilant container, a vaporizer may vaporize and activate the extracted sterilant, and a main needle may inject the vaporized sterilant into the vacuum pouch. Accordingly, a separate sterilant cartridge may be removed. The sterilant container may be formed at a portion recessed in the sterilant cartridge and may be sealed with a stopper made of a material such as silicone rubber having elasticity. When the sterilant container stores a sterilant such as hydrogen peroxide and is sealed with the stopper, after about a week, the hydrogen peroxide may be decomposed into water and oxygen and the oxygen may increase internal pressure of the sterilant container. Accordingly, sealing ability of the stopper is lowered by a strong pressure, and the hydrogen peroxide leaked through a gap of the stopper may peel off the vacuum pouch covering the stopper. Therefore, in order to solve the peeling problem by the hydrogen peroxide, a sealing film may seal the sterilant container by thermocompression. Thereby, a peeling phenomenon by the leakage of the hydrogen peroxide may be suppressed.

According to an embodiment of the present disclosure, the sterilant container may be firstly sealed using a sealing film having moisture impermeability, then secondarily sealed through an elastic stopper, and thirdly sealed by a vacuum pouch. The sealing film may be a laminated film of a polyethylene (PE) film/polyethylene terephthalate (PET) film. The PE film is formed of the same material as that of the sterilant cartridge and may improve thermocompression performance. In addition, the PET film may have lower moisture permeability than the PE film. Accordingly, the sterilant is sealed by the sealing film and may be maintained for a long time.

An auxiliary needle, which has a sharp tip, punctures the stopper and the sealing film to extract the sterilant contained in the sterilant container. When the auxiliary needle is removed, the stopper fills the space punctured by the auxiliary needle by elasticity, thereby preventing the remaining sterilant from leaking to the outside. The extracted sterilant is vaporized through a vaporizer and injected into the vacuum pouch by the main needle to perform a sterilization process.

According to an embodiment of the present disclosure, as a sterilant is stored in a sterilant cartridge, an appropriate amount of sterilant is stored relative to the volume of a packaging container. The sterilant is sealed with a non-permeable sealing film and again with an elastic body such as silicone. Accordingly, the sterilant may be stored stably for a long time. In addition, in a process of extracting the sterilant contained in the sterilant cartridge, no leakage of the sterilant may occur, thereby ensuring user safety and reliability of the sterilization process.

In addition, it is possible to perform a reliable sterilization process by transmitting information about the amount of sterilant injected by using code such as a bar code or a QR code printed on a pouch or a sterilant cartridge, the type of packaging container, date of manufacture, etc. to a sterilizer. Furthermore, warning information may be displayed when a used vacuum pouch is loaded again into a sterilization chamber by using information such as a bar code. Also, the information such as a bar code may be used to set a process mode according to this information.

Hereinafter, embodiments of the present disclosure will be described in detail with reference to the accompanying drawings. Advantages and features of the present disclosure, and implementation methods thereof will be clarified through following embodiments described with reference to the accompanying drawings. The present disclosure may, however, be embodied in many different forms and should not be construed as limited to the embodiments set forth herein. Rather, these embodiments are provided so that this disclosure will be thorough and complete, and will fully convey the concept of the present disclosure to one of ordinary skill in the art, and the present disclosure is only defined by the scope of claims.

Figure 2:
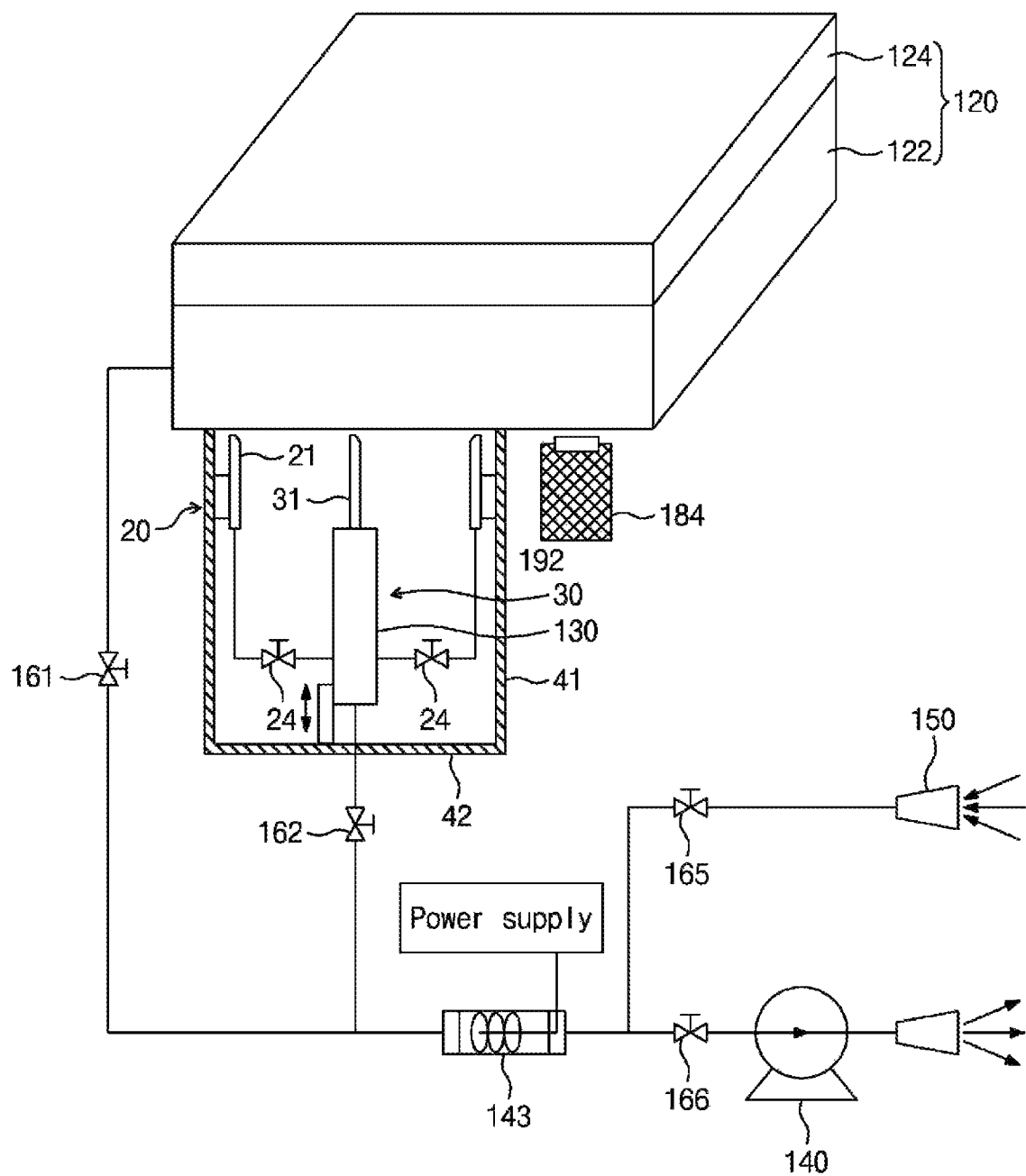
Figure 3:
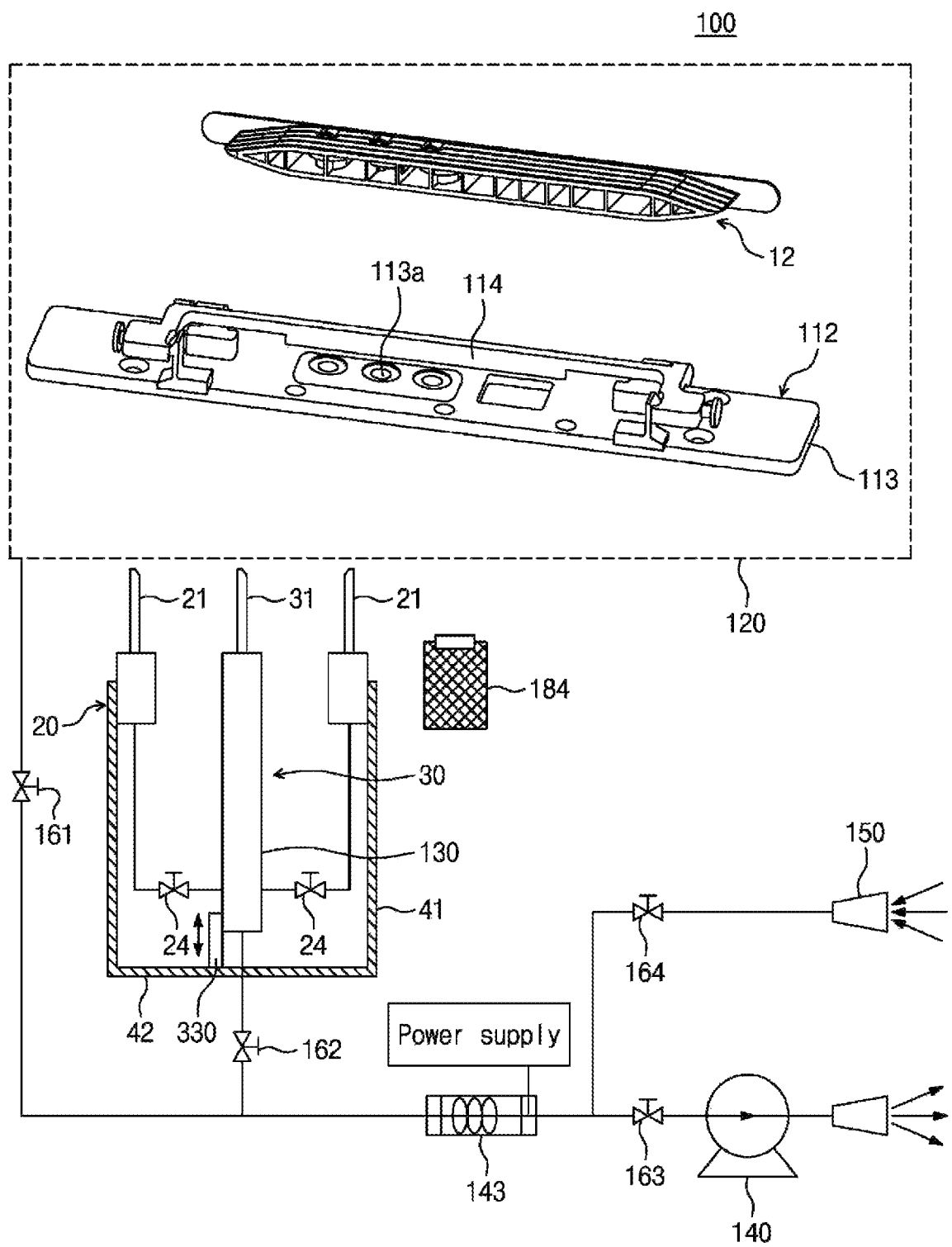

FIGS. 1 to 3 are conceptual diagrams of a sterilization apparatus according to an embodiment of the present disclosure.

Figure 4:
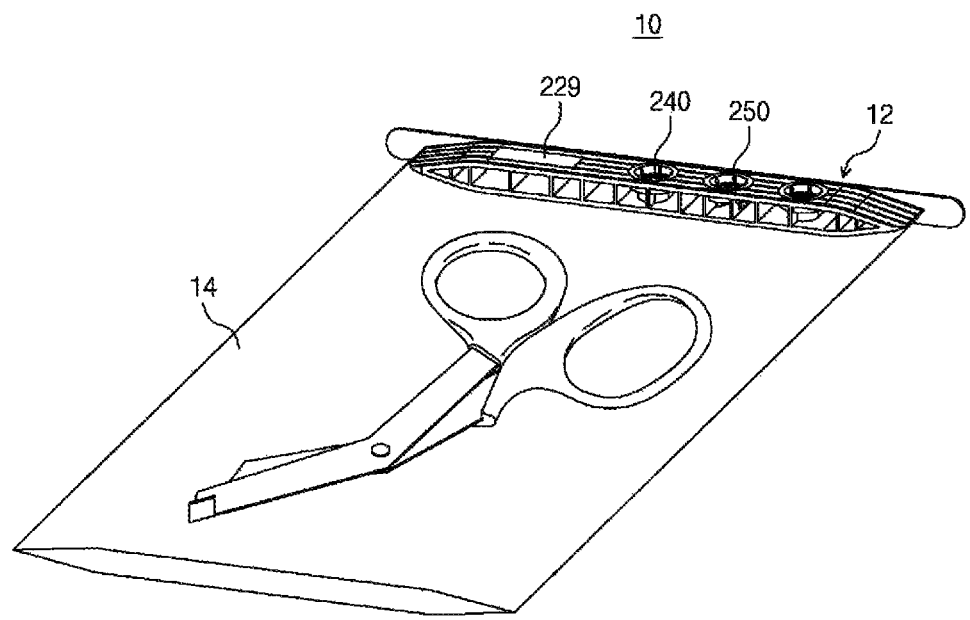
FIG. 4 is a perspective view of a vacuum pouch of the sterilization apparatus of FIG. 1.

FIG. 4 is a perspective view of a vacuum pouch of the sterilization apparatus of FIG. 1.

Figure 5:
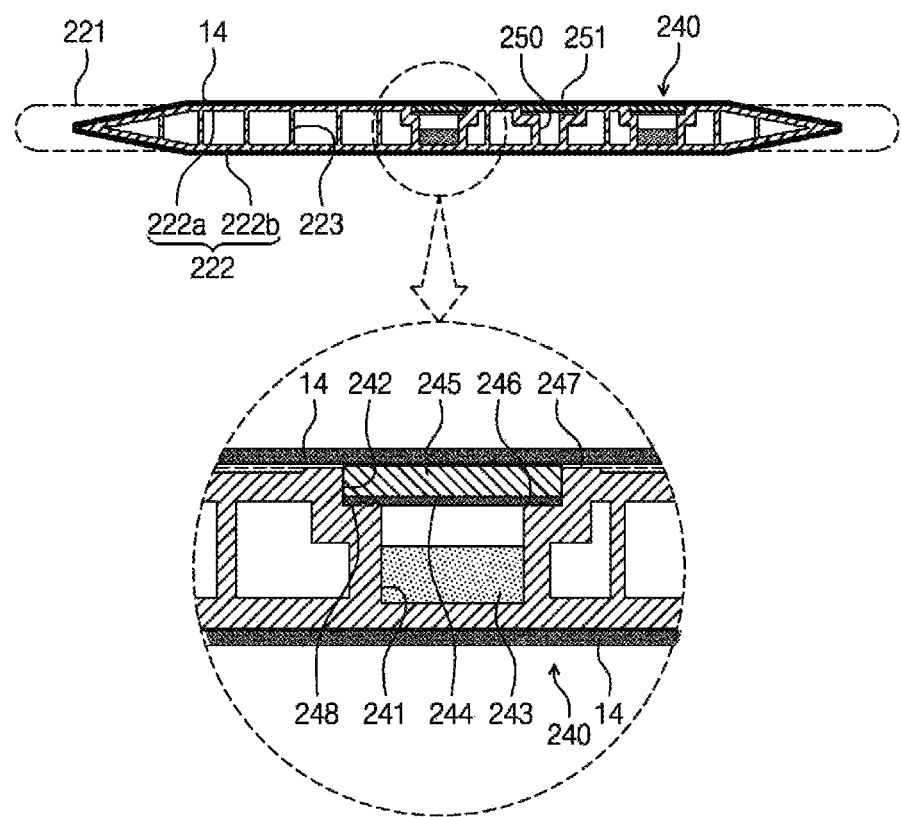
FIG. 5 is a cross-sectional view of a sterilant cartridge of the vacuum pouch of FIG. 4.

FIG. 5 is a cross-sectional view of a sterilant cartridge of the vacuum pouch of FIG. 4.

Figure 6:
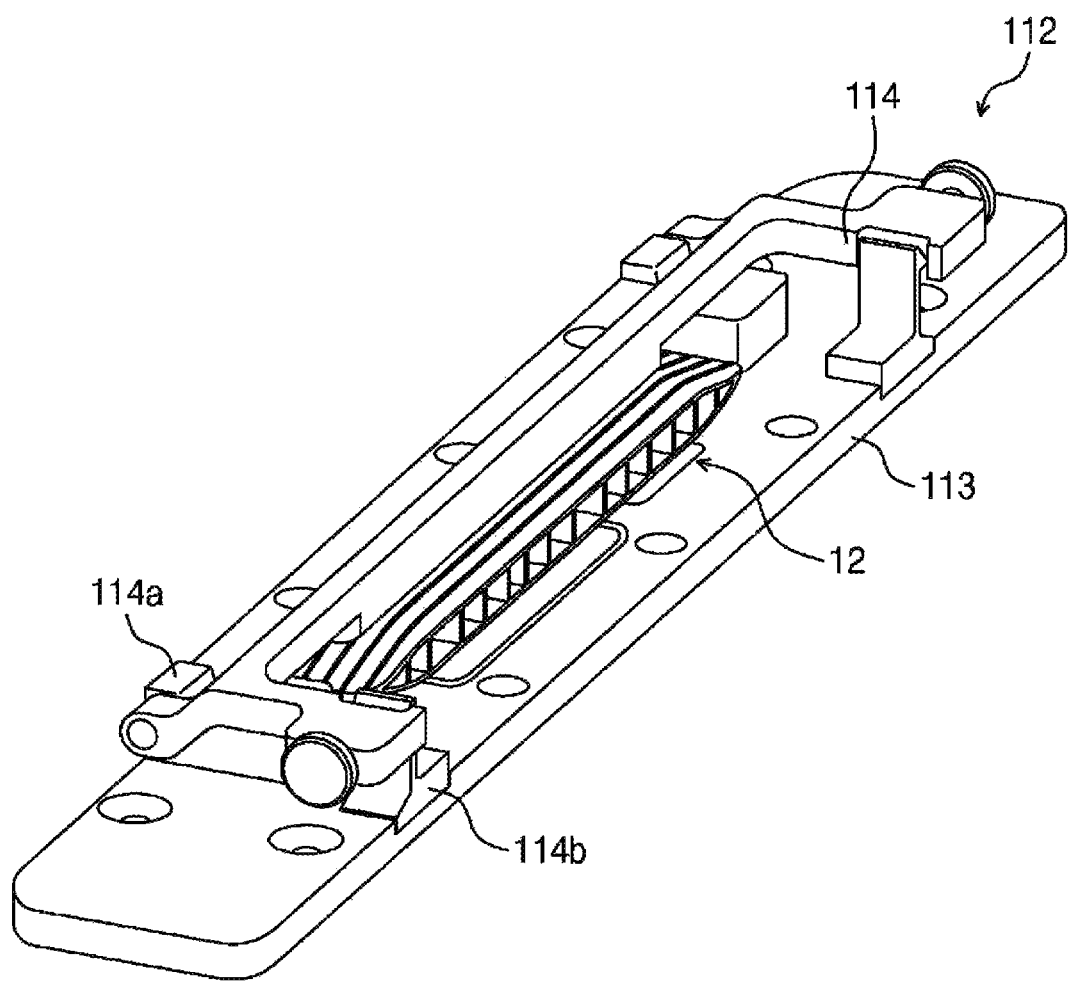
FIG. 6 is a perspective view of a heating block of the sterilization apparatus of FIG. 1.

FIG. 6 is a perspective view of a heating block of the sterilization apparatus of FIG. 1.

Figure 7:
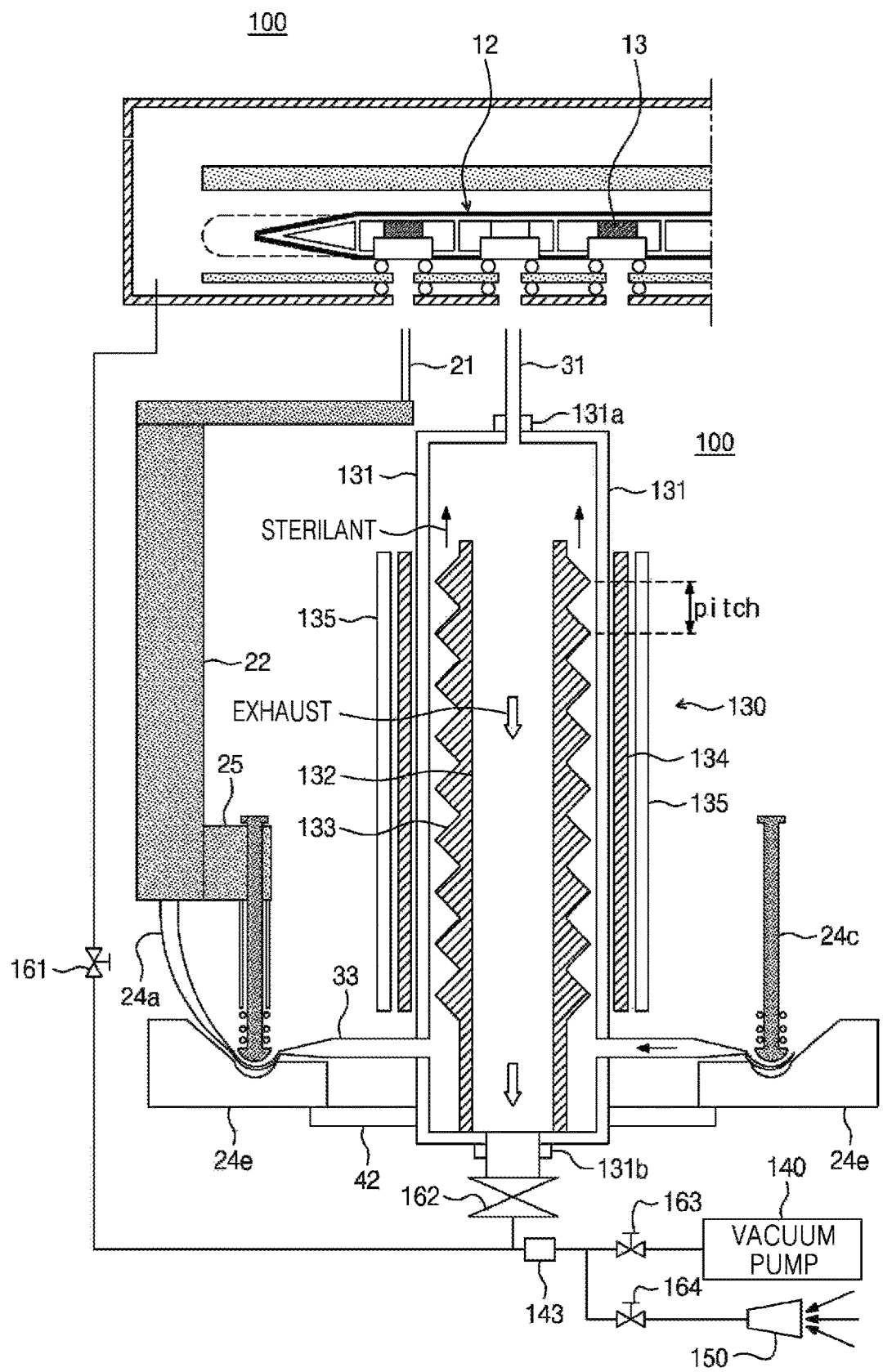
FIG. 7 is a conceptual diagram of a vaporizer of the sterilization apparatus of FIG. 1.

FIG. 7 is a conceptual diagram of a vaporizer of the sterilization apparatus of FIG. 1.

Figure 8:
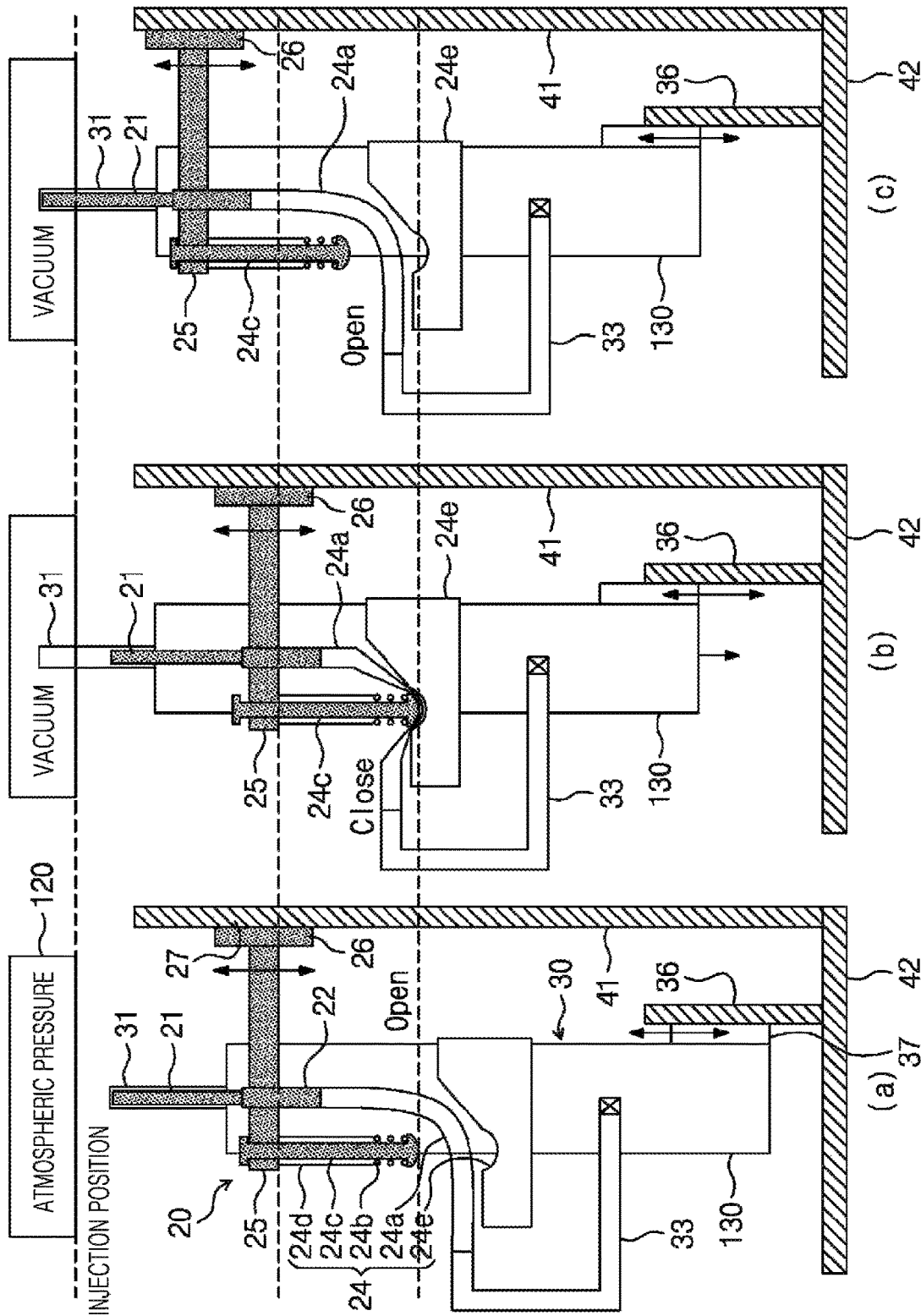
FIG. 8 is a conceptual diagram of a sterilant extractor and a sterilant supplier of FIG. 1.

FIG. 8 is a conceptual diagram of a sterilant extractor and a sterilant supplier of FIG. 1.

Figure 9:
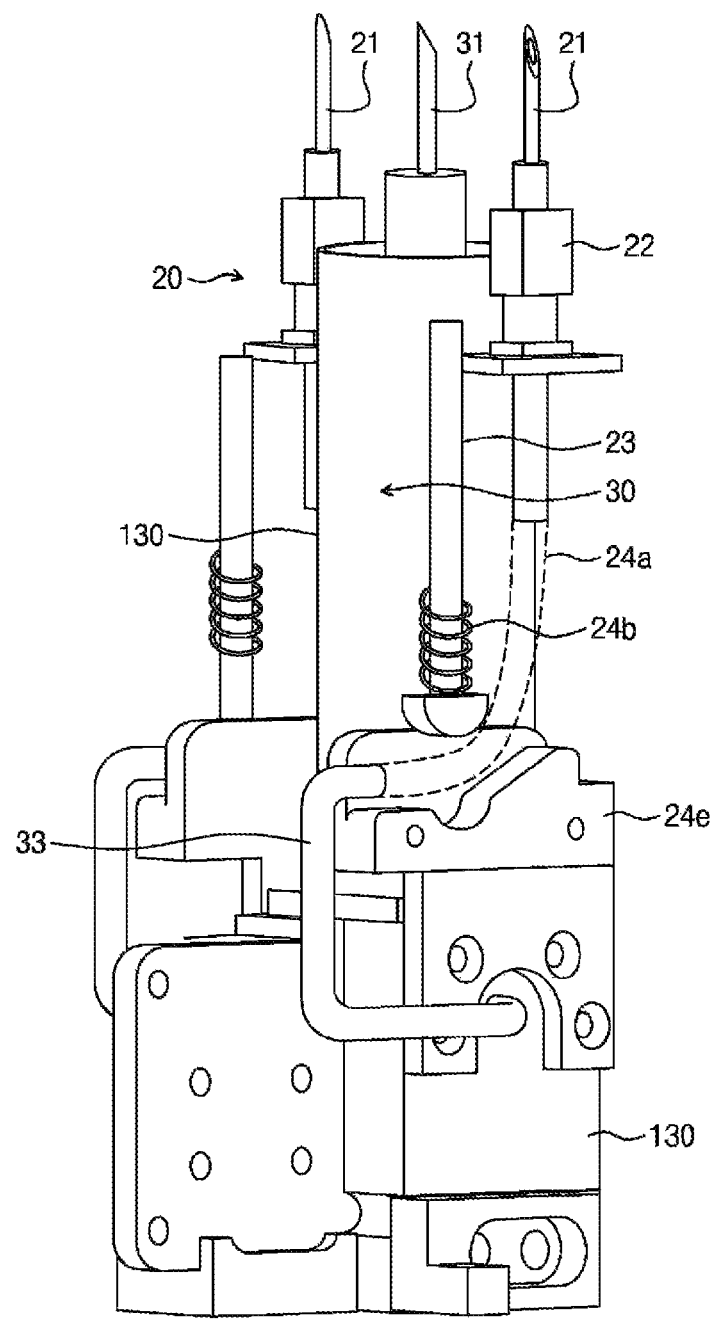
FIGS. 9 to 11 are perspective views of the sterilant extractor and the sterilant supplier of FIG. 1.
Figure 10:
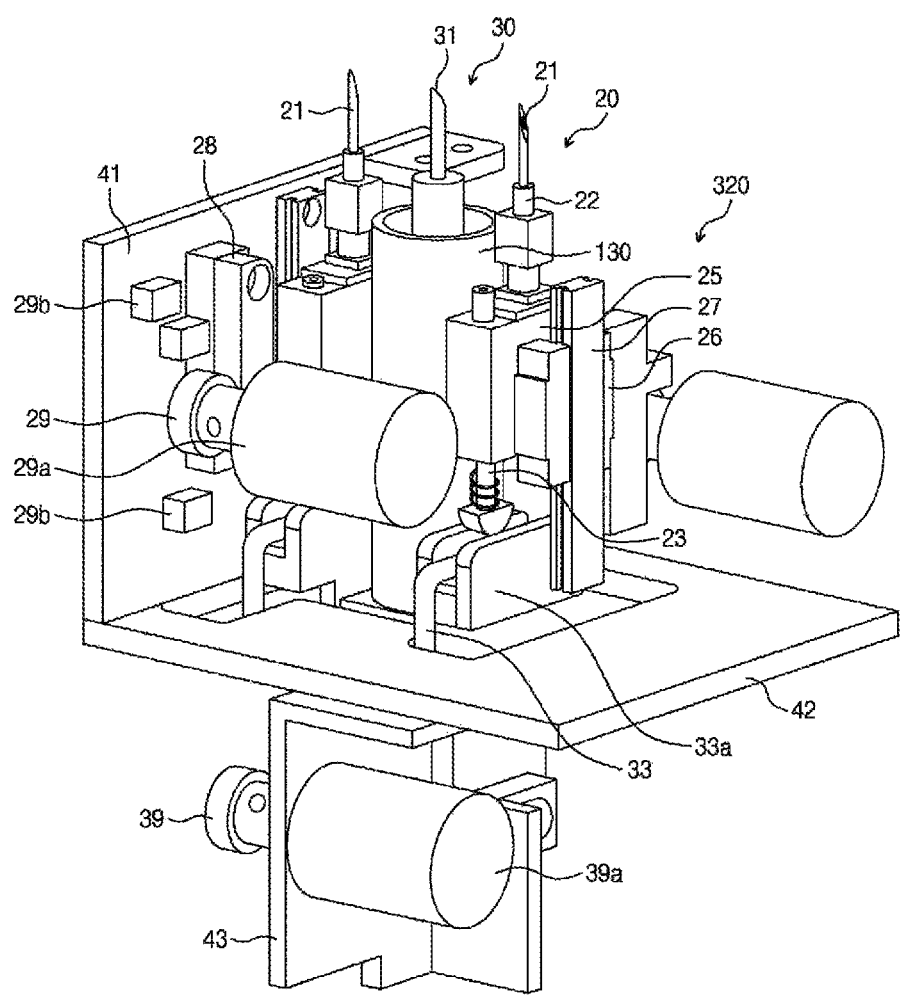
Figure 11:
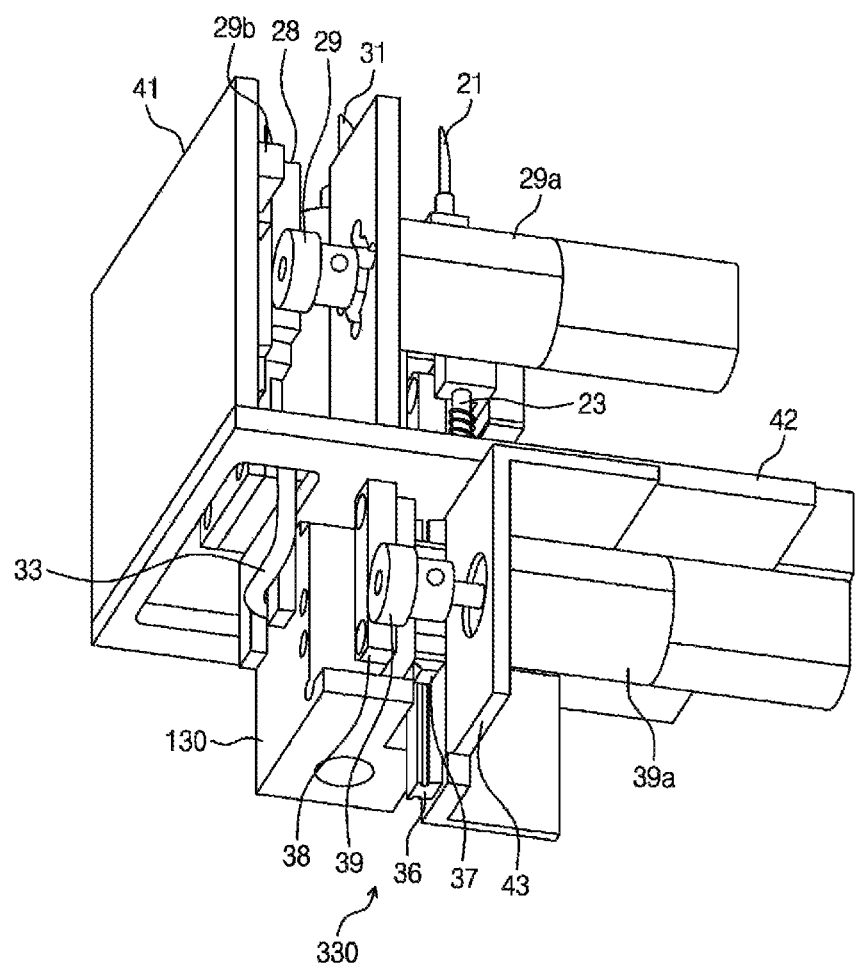

FIGS. 9 to 11 are perspective views of the sterilant extractor and the sterilant supplier of FIG. 1.

Referring to FIGS. 1 to 11, a sterilization apparatus 100 includes: a sterilant extractor 20 extracting a sterilant 243 using an auxiliary needle 21 from a sterilant cartridge 12 disposed inside or outside a sterilization chamber 120; and a sterilant supplier 30 which receives the sterilant extracted through the auxiliary needle, vaporizes the sterilant through a vaporizer, and provides the vaporized sterilant to the sterilization chamber or a vacuum pouch disposed inside the sterilization chamber through a main needle. The sterilant extractor 20 and the sterilant supplier 30 are disposed outside the sterilization chamber 120. A sterilant supply valve 24 is between the auxiliary needle 21 and the sterilant supplier 30 to adjust the sterilant extracted from the sterilant cartridge 12 to be supplied to the sterilant supplier 30. The sterilant extractor 20 and the sterilant supplier 30 may be disposed in a housing coupled to a lower surface of the sterilization chamber. The housing may include a sidewall 41 and a lower plate 42.

The sterilization apparatus 100 includes: a vacuum pouch 10 having a vacuum packaging bag 14 that is sealed to store a target object therein and to be kept in a vacuum state and the sterilant cartridge 12 for containing a sterilant and injecting the sterilant into the vacuum packaging bag 14; the sterilization chamber 120 having a door 124 and accommodating the vacuum pouch; needles 21 and 31 for extracting the sterilant contained in the sterilant cartridge, injecting the extracted sterilant into the vacuum pouch 10, and vacuum evacuating the vacuum pouch; and a vacuum pump 140 for exhausting the vacuum pouch 10 and the sterilization chamber 120.

The sterilant cartridge 12 includes a sterilant container 240 sealed to contain the sterilant and a sterilant injection path 250. The vacuum packaging bag 14 is thermocompressed with the sterilant cartridge 12 and stores the target object.

The sterilant container 240 includes: a sterilant containing space 241 for containing the sterilant 243; a sterilant stopper accommodating space 242 continuously connected to an upper surface of the sterilant containing space 241 and having a larger area than the upper surface of the sterilant containing space; a sealing film 244 for sealing an interface between the sterilant containing space 241 and the sterilant stopper accommodating space 242; and a sterilant stopper 245 disposed in the sterilant stopper accommodating space and having elasticity.

The sterilant 243 extracted from the sterilant container 240 is injected into the vacuum packaging bag 14 through the sterilant injection path 250 to sterilize the target object.

The sterilization chamber 120 may include the door 124 and a chamber body 122. The door 124 may be a cover of the sterilization chamber 120. The door 124 may be coupled to the sterilization chamber 120 by a rotating unit such as a hinge. The sterilization chamber 120 may provide an environment in which the vacuum pouch 10 is expanded to secure a constant internal volume by removing a pressure difference between the inside and the outside of the vacuum pouch 10.

The needles 21 and 31 may include the auxiliary needle 21 for extracting a sterilant and the main needle 31 for injecting the extracted sterilant into the vacuum pouch through the sterilant injection path.

The sterilization chamber 120 may have a space for accommodating the vacuum pouch 10 and a heating block 112 therein. The sterilization chamber 120 may have a rectangular parallelepiped shape and may be formed of metal.

The sterilization chamber 120 may be connected to the vacuum pump 140 through a connection pipe. The vacuum pump 140 may vacuum evacuate the vacuum chamber 120 and the vacuum pouch 10.

A filter 150 may suck in the air to remove fine dust and bacteria and provide the air to the sterilization chamber 120 or the vacuum pouch 10.

A vaporizer 130 may receive the sterilant contained in the sterilant cartridge 12 to vaporize the sterilant and inject the sterilant into the vacuum pouch 10. When the sterilant is hydrogen peroxide, the vaporizer 130 may heat and vaporize the sterilant at a temperature of 50° C. to 110° C. and may inject the vaporized sterilant into the vacuum pouch 10 through the sterilant cartridge 12. The vaporizer 130 may be disposed outside the sterilization chamber 120. The vaporizer 130 may be provided with a sterilant of the sterilant container 240 through the auxiliary needle 21.

The heating block 112 may be disposed in the vacuum chamber 120 and may contact the sterilant injection block 12 to heat the sterilant injection block 12. The heating block 112 is heated from 50° C. to 110° C. and may heat some or the entire vacuum pouch 10. The heating block 112 may be mounted on the lower surface of the sterilization chamber 120 and may vertically move to apply pressure to the sterilant cartridge 12. The heating block 112 may include a lower heating block 113 for aligning the sterilant cartridge 12 and an upper heating block 114 for pressing and holding the sterilant cartridge from the top. The upper heating block 114 may rotate through a pair of hinges 114a. The upper heating block 114 may be coupled to a fastening member 114b mounted on the lower heating block 113 to provide a locked/released state. The lower heating block 113 may include a through hole 113a through which a needle may pass.

When the sterilization chamber 120 is vacuum evacuated, heat transfer through the air is impossible. Therefore, the heating block 112 may be pressed in direct contact with the vacuum pouch 10 or the sterilant cartridge 12. The inside of the heating block 112 may be heated by a heat wire. The heating block 112 may press and heat the sterilant injection block 12 of the vacuum pouch 10. The heating block 112 may be on the lower surface of the sterilization chamber 120 to align and support the sterilant cartridge. In addition, the lower heating block 113 may have a plate shape and may include a plurality of through holes 113a to allow the needles 21 and 31 to access the sterilant cartridge 12.

The heating block 112 may be fixed to the lower surface of the sterilization chamber 120. The lower heating block 113 may support the vacuum pouch and provide a through hole through which the main needle 31 may pass. A sealing member on an upper surface of the lower heating block 113 may contact the sterilant cartridge 12 to seal around the sterilant container 240 and around the sterilant injection path 250. The sealing unit may be an O-ring. A sealing member on a lower surface of the lower heating block 113 may be in contact with the lower surface of the sterilization chamber 120 to seal around the through hole.

The sealing member on the upper surface of the lower heating block 113 may contact the sterilant cartridge to seal around the sterilant stopper 245 and around a sterilant injection path stopper 251. The sealing unit may be an O-ring.

The main needle 31 may be disposed to pass through the through hole for the main needle of the lower heating block 113. An end of the main needle 31a is obliquely processed like a typical needle, and an opening (not shown) may be formed in a side surface of the end of the main needle 31. A fluid path may be provided through an opening of the main needle 31. The main needle 31 may provide a path for exhausting air from the vacuum pouch 10 and may provide a path for supplying a sterilant from the outside to the inside of the vacuum pouch 10. An inner diameter of the main needle 31 may be at least 0.5 mm or more. The inner diameter of the main needle may be sufficiently short and large to provide sufficient conductance for vacuum evacuation. A length of the main needle 31 may be a few centimeters or less and the inner diameter of the main needle 31 may be 0.5 mm or more. A material of the main needle may be metal or a metal alloy. A main needle transfer portion 330 may provide vertical linear motion to a main needle 194a and may be disposed outside the sterilization chamber 120.

The auxiliary needle 21 may extract the sterilant 243 contained in the sterilant cartridge 12. The auxiliary needle 21 may extract a liquid sterilant contained in the sterilant container 240 of the sterilant cartridge. An auxiliary needle transfer portion 320 may provide vertical linear motion to the auxiliary needle 21 and may be disposed outside the sterilization chamber 120. The auxiliary needle may have the same structure and shape as the main needle.

The vacuum pouch 10 includes: the sterilant cartridge 12 having the sterilant container 240 sealed to contain a sterilant and the sterilant injection path 250; and the vacuum packaging bag 14 that is thermocompressed with the sterilant cartridge and contains a target object. The sterilant container 240 includes: the sterilant containing space 241 for containing the sterilant; a sterilant stopper accommodating space 242 continuously connected to an upper surface of the sterilant containing space and having a larger area than the upper surface of the sterilant containing space; the sealing film 244 for sealing an interface between the sterilant containing space and the sterilant stopper accommodating space; and a sterilant stopper 235 disposed in the sterilant stopper accommodating space and having elasticity. The sterilant extracted from the sterilant container is injected into the vacuum packaging bag through the sterilant injection path to sterilize the target object.

The vacuum pouch 10 is made of a nylon (NY) and/or PE material having sufficient flexibility and may be in the form of a bag sealed in a film form. The vacuum pouch 10 may include the vacuum packaging bag 14 accommodating a target object and the sterilant cartridge 12 disposed at one end of the vacuum packaging bag 14. The other end of the vacuum packaging bag 14 is initially opened, and after a target object (e.g., a medical device) is inserted, may be sealed by a method such as thermocompression to form a thermocompression bonding strip. The vacuum pouch 10 may include the sterilant cartridge 12 for vacuum evacuation and injecting a sterilant from the outside. The sterilant cartridge may include at least one sterilant container 240 for containing a fixed amount of sterilant. The sterilant container 240 may be installed in the sterilant cartridge 12. The vacuum packaging bag 14 may be made of polyethylene. The vacuum packaging bag 14 may include a lower film and an upper film which provide an internal space.

The sterilant cartridge 12 may include a PE material that is the same material as that of the vacuum packaging bag 14. Accordingly, the sterilant cartridge 12 may be sealed with the vacuum packaging bag 14 by thermocompression. The material of a surface of the sterilant cartridge 12 may be the same as the material of the vacuum packaging bag. Accordingly, the sterilant cartridge 12 may be thermocompressed with the vacuum packaging bag 14 to provide a sealed space.

The sterilant container 240 includes: the sterilant containing space 241 for containing the sterilant; the sterilant stopper accommodating space 242 continuously connected to the upper surface of the sterilant containing space 241 and having a larger area than the upper surface of the sterilant containing space; the sealing film 244 for sealing an interface between the sterilant containing space 241 and the sterilant stopper accommodating space 242; and the sterilant stopper 245 disposed in the sterilant stopper accommodating space and having elasticity. The sterilant 243 extracted from the sterilant container by the auxiliary needle is injected into the vacuum packaging bag 14 through the main needle and the sterilant injection path 250 to sterilize the target object.

The sterilant cartridge 12 may include: an upper strip 222a and a lower strip 222b having opposite ends bent to contact each other and the central portions extending parallel to each other; a barrier wall 223 between the upper strip and the lower strip; the sterilant injection path stopper 251 on the upper strip to block the sterilant injection path 250; and an alignment strip 221 extending laterally along one side of the upper strip 222a and the lower strip 222b to seal the one side of the upper strip and the lower strip. The sterilant injection path 250 penetrates through the upper strip 222a and is exposed to the opposite side of the alignment strip 221, and the sterilant container 240 may be recessed in an upper surface of the upper strip 222a and disposed between the upper strip 222a and the lower strip 222b. The upper surface of the upper strip 222a and a lower surface of the lower strip 222b may be thermocompressed with each other at one end of the vacuum packaging bag 14.

The sterilant stopper 245 and the sterilant injection path stopper 251 may be made of an elastic material such as silicone rubber. The sterilant stopper 245 and the sterilant injection path stopper 251 may be fixed by fitting and/or an adhesive. Thus, even when the needle punctures the sterilant stopper 245 and the sterilant injection path stopper 251 and then retreats, the sterilant stopper 245 and the sterilant injection path stopper 251 may sufficiently seal the vacuum pouch. After the sterilization process is completed, even when the vacuum pouch is exposed to the polluted atmosphere for a long time, the sterilant injection path stopper 251 may prevent infiltration of bacteria. The sterilant stopper 245 may suppress leakage of the remaining sterilant. An upper surface of the sterilant stopper 245 and the sterilant injection path stopper 251 may protrude about 0.1 mm from the upper surface of the upper strip 222a. When the vacuum packaging bag and the upper strip 222a are thermocompressed with each other, the vacuum packaging bag may apply pressure to the sterilant stopper 245. Accordingly, sealing ability of the sterilant stopper 245 may be improved.

The main needle 31 may puncture the sterilant injection path stopper 251. A material of the sterilant injection path stopper 251 may be silicone rubber or an elastic polymer material. When the main needle 31 punctures the sterilant injection path stopper 251, the sterilant injection path stopper 251 may maintain a sealed state by elasticity. When fluid flows through the main needle 31, the fluid may not leak through the sterilant injection path stopper 251. In addition, when exhausting the inside of the vacuum pouch through the main needle 31, the sterilant injection path stopper 251 may maintain sufficient vacuum sealing.

The sterilant containing space 241 for containing the sterilant may be a space disposed adjacent to the lower strip 222b between the upper strip 222a and the lower strip 222b. The sterilant accommodating space 241 may be cylindrical in shape.

The sterilant stopper accommodating space 242 may be a space disposed adjacent to the upper strip 222a. The sterilant stopper accommodating space 242 may be aligned vertically with the sterilant containing space 241 and have a larger cross-sectional area.

When the sterilant containing space 241 is sealed with only a sterilant stopper made of an elastic material, hydrogen peroxide contained in the sterilant containing space 241 may expand and leak from a gap between the sterilant stopper 245 and the sterilant stopper accommodating space 242 to peel off the thermocompressed vacuum pouch. In order to solve this problem, the sealing film 244 may seal the interface between the sterilant containing space 241 and the sterilant stopper accommodating space 242. The sealing may be performed by thermocompression. For efficient thermocompression sealing, the sealing film 244 may be the laminated film of the PE film/PET film. The PE film of the sealing film 244 may be thermocompression-bonded to a lower surface of the sterilant stopper accommodating space 242 of a PE material. The lower surface of the sterilant stopper accommodating space 242 may have a protruding thermocompression ring 246 in the form of a ring.

Each of the upper strip 222a and the lower strip 222b may include a plurality of thermocompression lines 231 extending in a length direction and protruding from the surface thereof. The thermocompression lines 231 may perform efficient thermocompression with the vacuum packaging bag 14.

The height of the upper strip 222a around an upper surface of the sterilant stopper accommodating space 242 may be equal to the height of the thermocompression lines 231. Accordingly, the vacuum packaging bag 14 may be efficiently thermocompressed around the upper surface of the sterilant stopper accommodating space 242.

In addition, the height of the upper strip 222a around an upper surface of the sterilant injection path 250 may be the same as the height of the thermocompression lines 231. As a result, the vacuum packaging bag 14 may be efficiently thermocompressed around the upper surface of the sterilant injection path 250.

A code adhesive tape 229 having code such as a bar code or a QR code to be printed may be attached to the vacuum pouch 10 or the sterilant cartridge 12. It is possible to perform a reliable sterilization process by transmitting information about the amount of sterilant injected by using the code adhesive tape 229, the type of packaging container, date of manufacture, etc. to the sterilizer. A code reader 184 may extract information of the code adhesive tape 229 through an opening formed in a support plate of a vacuum pouch supporter 182.

The sterilization apparatus 100 may include a plurality of valves 161 to 164. The valves 161 to 164 may be used to exhaust the vacuum pouch 10 and the sterilization chamber 120, to inject a sterilant into the vacuum pouch 10, and to vent the vacuum pouch 10 and the sterilization chamber 120 to the atmosphere.

The vaporizer 130 includes: a cylindrical vaporizer body tube 131 including a first connection port 131a connected to the main needle 31 and a second connection port 131b connected to the vacuum pump 140; a heater 134 disposed to surround the evaporation body tube 131; a main pipe 132 inserted into the vaporizer body tube 131; a conductance adjuster 133 between the vaporizer body tube 131 and the main pipe 132; and a sterilant supply pipe 33 connected to a lower side of the vaporizer body tube 131. A liquid sterilant supplied through the sterilant supply pipe 33 is evaporated between the vaporizer body tube 131 and the main pipe 132 to move along the conductance adjuster 133 and is discharged to an inner upper portion of the vaporizer body tube 131.

The sterilization chamber 120 may be connected to the vacuum pump 140 through an exhaust pipe and the first valve 161. The vacuum pump 140 may vacuum evacuate the sterilization chamber 120. The sterilization chamber 120 may provide an environment that may vary the volume of the vacuum pouch 10.

The vacuum pouch 10 is made of a NY and/or PE material having sufficient flexibility and may be in the form of a bag sealed in a film form. The vacuum pouch 10 may include a vacuum packaging bag 14 and the sterilant cartridge 12 disposed at one end of the vacuum packaging bag. The sterilant cartridge 12 may provide a vacuum evacuation path and a sterilant injection path. The sterilant cartridge 12 may perform vacuum evacuation and sterilant injection through the sterilant injection path stopper 251.

The other end of the vacuum pouch 10 is initially opened, and after a target object (e.g., a medical device) is inserted, may be sealed by a method such as thermocompression to include a thermocompression bonding strip. The vacuum pouch 10 may include the sterilant cartridge 12 for vacuum evacuation and injecting a sterilant from the outside. The vacuum packaging bag 14 may be made of polyethylene. The vacuum packaging bag 14 may include a lower film and an upper film which provide an internal space by edge thermocompression.

The vaporizer 130 may vaporize a sterilant and inject the vaporized sterilant into the vacuum pouch 10 and may provide a vacuum evacuation path and an external air injection path. When the sterilant is hydrogen peroxide, the vaporizer 130 may heat and vaporize the sterilant at a temperature of 50° C. to 110° C. and may inject the vaporized sterilant into the vacuum pouch 10. The vaporizer 130 may be disposed outside the vacuum chamber 120. The vaporizer 130 may include the vaporizer body tube 131, the heater 134, the main pipe 132, the conductance adjuster 133, and the sterilant supply pipe 33. The vaporizer 130 may have a coaxial double tube structure including the vaporizer body tube 131 and the main pipe 132.

The vaporizer body tube 131 may include one pipe or a plurality of pipes continuously connected to each other. The vaporizer body tube 131 may be cylindrical in shape. When the vaporizer body tube 131 includes a plurality of pipes, the plurality of pipes may be disassembled from each other to replace the main pipe 132 in the vaporizer body tube 131. When impurities included in the sterilant are deposited on an outer surface of the main pipe 132, the conductance may be changed to prevent stable sterilant supply. In order to remove the impurities, the main pipe 132 may be replaced or cleaned.

The heater 134 may heat the vaporizer body tube 131 through a heating member such as a heat wire. Accordingly, the vaporizer body tube 131 may vaporize the liquid sterilant. A controller may sense a temperature of the vaporizer body tube 131 through a temperature sensor mounted on an outer circumferential surface of the vaporizer body tube and control the heater 134 to maintain a set temperature.

The conductance adjuster 133 may be between the main pipe 132 and the vaporizer body tube 131. The conductance adjuster 133 may provide conductance sufficiently less than conductance defined by an inner diameter of the main pipe 132. Accordingly, the main pipe 132 may function as a vacuum pumping line and a venting line. In addition, the conductance adjuster 133 may provide a sufficient residence time and vaporize the liquid sterilant by using a low conductance due to a spiral fluid path. The conductance adjuster 133 may be a thread formed on an outer circumferential surface of the main pipe 132. The thread may provide a moving path of a sterilant that is long relative to a straight distance. A pitch of the thread may be between about 0.5 mm and about 1.5 mm to remove air or a sterilant in a space between the main pipe 132 and the vaporizer body tube 131 and to provide a sterilant injection path. Since an increase in the pitch of the thread increases conductance, when the increase in the pitch of the thread is out of a certain range, a residence time of the sterilant may be reduced so that the sterilant may not be sufficiently vaporized. In addition, a decrease in the pitch of the thread increases conductance, which may make vacuum treatment difficult in the sterilant supply pipe.

The sterilant supply pipe 33 may be connected to a lower surface of the vaporizer body tube 131. The sterilant supply pipe 33 may have a constant distance from the second connection port 131b. A lower surface of the main pipe 132 may be coupled to the lower surface of the vaporizer body tube and sealed. Accordingly, a liquid sterilant flowing into the sterilant supply pipe 33 may be temporarily contained and prevented from flowing out through the lower surface of the main pipe 132.

The sterilant supply valve 24 may include: an elastic pipe 24a of elastic material disposed between the auxiliary needle and the vaporizer; and a compressor pressing and closing the elastic pipe. The compressor may include: a pressing head 24c for pressing the elastic pipe locally; an elastic spring 24b disposed to surround a lower side surface of the pressing head; a pressing head pipe 24d disposed to surround an upper side surface of the pressing head; and a pressing head receiver 24e recessed locally to receive the pressing head 24c and fixed to the vaporizer 130. The elastic spring 24b may have a larger elastic modulus to provide sufficient pressure to the elastic pipe.

The sterilant supply pipe 33 may connect the vaporizer 130 to the elastic pipe 24a. One end of the sterilant supply pipe 33 may be connected to the vaporizer, and the other end of the sterilant supply pipe 33 may be bent to extend in a direction perpendicular to a moving direction of the pressing head 24c. The elastic pipe 24a may be bent into an "L" shape.

The auxiliary needle 21 may supply a liquid sterilant to the sterilant supply pipe 33 through the sterilant supply valve 24. The auxiliary needle 21 may provide the sterilant in the form of a pulse or continuously through the sterilant supply pipe 33 to a space between the vaporizer body tube 131 and the main pipe 132.

The auxiliary needle 21 may be plural, and thus, the sterilant supply pipe 33 may be plural. The sterilant supply pipe 33 may be disposed symmetrically with respect to the vaporizer body tube 131.

The second connection port 131b of the vaporizer body tube 131 may be connected to the vacuum pump 140 through the second valve 162. In addition, the sterilization chamber 120 may be connected to the vacuum pump through the separate first valve 161. The third valve 163 may be at a front end of the vacuum pump, and the fourth valve 164 may be at a front end of the filter 150. The first valve, the second valve, the third valve, and the fourth valve may be connected to a first node N1.

The sterilant extractor 20 may include the auxiliary needle 21 and a pipe connected to the auxiliary needle. The sterilant supplier 30 may include the main needle 31 and the vaporizer 130.

The auxiliary needle transfer portion 320 may linearly move the sterilant extractor 20 so that the auxiliary needle 21 punctures the sterilant cartridge 12 to extract the sterilant. The auxiliary needle transfer portion 320 may include: an auxiliary needle supporter 22 supporting the auxiliary needle 21; an auxiliary needle transfering body 25 fixing the auxiliary needle supporter 22 and the compressor; an auxiliary needle slide 26 fixedly coupled to the auxiliary needle transfering body 25 and performing linear motion; an auxiliary needle linear motion guide 27 guiding the auxiliary needle slide 26; a rack gear 28 providing a driving force to the auxiliary needle transfering body; a pinion gear 29 in gear engagement with the rack gear; and a motor 29a rotating a central axis of the pinion gear. The secondary needle linear motion guide 26 may be fixed to the sidewall 41. The sidewall may be fixedly coupled to the sterilization chamber.

The main needle transfer portion 330 may linearly move the sterilant supplier 30 so that the main needle 31 communicates with the sterilant injection path disposed in the sterilant cartridge. The main needle transfer portion 330 may include: a main needle slide 37 fixedly coupled to the vaporizer 130 and performing linear motion; a main needle linear motion guide 36 guiding the main needle slide; a rack gear 38 providing a linear motion driving force to the vaporizer; a pinion gear 39 in gear engagement with the rack gear; and a motor 39a rotating a central axis of the pinion gear. The main needle linear motion guide 36 may be fixed to the lower plate 42.

A plasma source 143 may decompose a sterilant discharged from the vacuum pouch 10, and the decomposed sterilant may be discharged to the outside through the vacuum pump 140. In addition, the plasma source 143 may discharge external air supplied through the filter 150 to provide an activated gas to the vacuum pouch 10 via the vaporizer 130.

The vaporizer 130 may include: a heat reflection tube 135 disposed to surround the heater 134; and an insulator disposed between the heater 134 and the heat reflection tube 135. The heat reflection tube may be a surface polished aluminum pipe.

Figure 12:
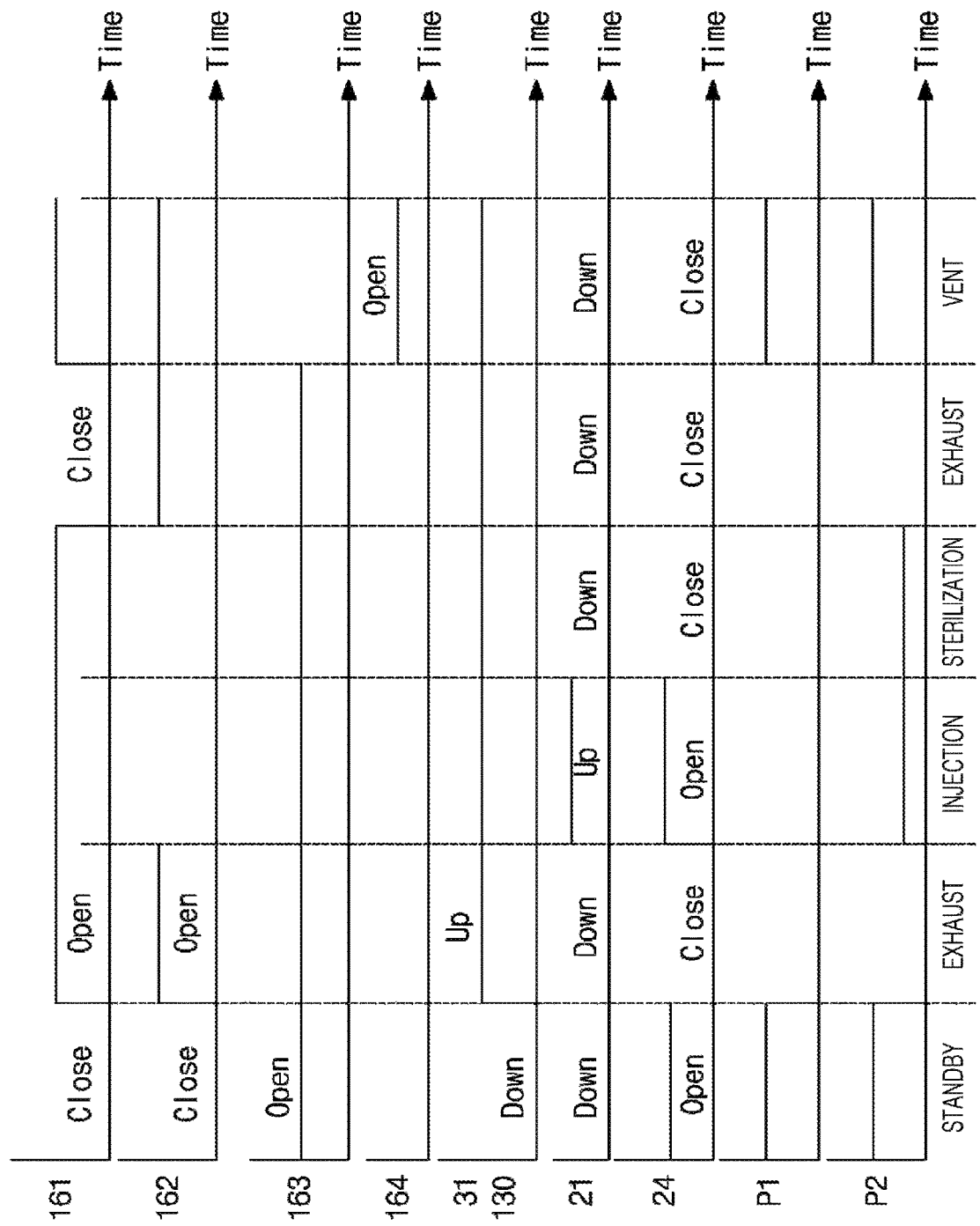
FIG. 12 is a view for explaining an operating method of the sterilization apparatus of FIG. 1.

FIG. 12 is a view for explaining an operating method of the sterilization apparatus of FIG. 1.

Referring to FIG. 12, the sterilization apparatus 100 includes: the sterilant extractor 20 extracting a sterilant using the auxiliary needle 21 from a sterilant cartridge disposed inside or outside a sterilization chamber; and the sterilant supplier 30 which receives the sterilant extracted through the auxiliary needle, vaporizes the sterilant through the vaporizer 130, and provides the vaporized sterilant to the sterilization chamber 120 or the vacuum pouch 10 disposed inside the sterilization chamber through the main needle 31. The operating method of the sterilization apparatus includes: vacuum evacuating a sterilization chamber or a vacuum pouch disposed in the sterilization chamber using a main needle while a connection path between the vaporizer and the auxiliary needle is closed; extracting a sterilant contained in the sterilant cartridge using the auxiliary needle and injecting the sterilant into the sterilization chamber or the vacuum pouch through the vaporizer while the connection path between the vaporizer and the auxiliary needle is opened; sterilizing a target object in the sterilization chamber or the vacuum pouch with the connection path between the vaporizer and the auxiliary needle closed; and exhausting the sterilant diffused in the sterilization chamber or the vacuum pouch. P1 refers to pressure in the vacuum pouch and P2 refers to pressure in the sterilization chamber.

An open/close state of the connection path between the vaporizer 130 and the auxiliary needle 21 may be determined by positions of the auxiliary needle 21 and the main needle 31. The open/close state of the connection path may be achieved by compression of the elastic pipe 24a. The open state of the connection path may be achieved when both the auxiliary needle and the main needle are raised to penetrate the sterilant cartridge 12.

The vacuum pouch 10 disposed in the sterilization chamber is vacuum evacuated using the main needle while the connection path between the vaporizer and the auxiliary needle is closed. In more detail, the first valve 161 is opened, the second valve 162 is opened, the third valve 163 is opened, and the fourth valve 164 is closed. The main needle transfer portion 330 raises the main needle 31 and the vaporizer 130. Accordingly, the main needle 31 exhausts the air inside the vacuum pouch 10 to the outside. In addition, the air of the sterilization chamber 120 is exhausted to the outside through the vacuum pump 140.

Subsequently, the sterilant contained in the sterilant cartridge is extracted by using the auxiliary needle 21 while the connection path between the vaporizer and the auxiliary needle is opened, and the sterilant is injected into the vacuum pouch 10 through the vaporizer 130. In more detail, the second valve 162 is closed, and the auxiliary needle transfer portion raises the auxiliary needle. The auxiliary needle extracts the sterilant from the sterilant cartridge and provides the sterilant to the vaporizer along the open sterilant supply valve 24, and the vaporizer vaporizes the sterilant and provides the same inside the vacuum pouch.

Subsequently, the target object is sterilized in the sterilization chamber or the vacuum pouch while the connection path between the vaporizer 130 and the auxiliary needle 21 is closed. In more detail, the auxiliary needle 21 is lowered by using the auxiliary needle transfer part 320, and the sterilant supply valve 24 is closed.

Subsequently, the sterilant diffused in the sterilization chamber or the vacuum pouch is exhausted. In more detail, the first valve 161 is closed. The sterilant, which has been sterilized in the vacuum pouch, is exhausted to the outside through the vacuum pump 140 by opening the second valve 162. The sterilant may be decomposed by the plasma source 143 at the front end of the vacuum pump and exhausted to the outside.

Subsequently, external air is injected into the sterilization chamber or the vacuum pouch and vented. In more detail, the first valve 161 is opened, and the second valve 162 is opened. The third valve 163 is closed. The fourth valve 164 is opened. Accordingly, the vacuum pouch and the sterilization chamber are vented to atmospheric pressure.

Figure 13:
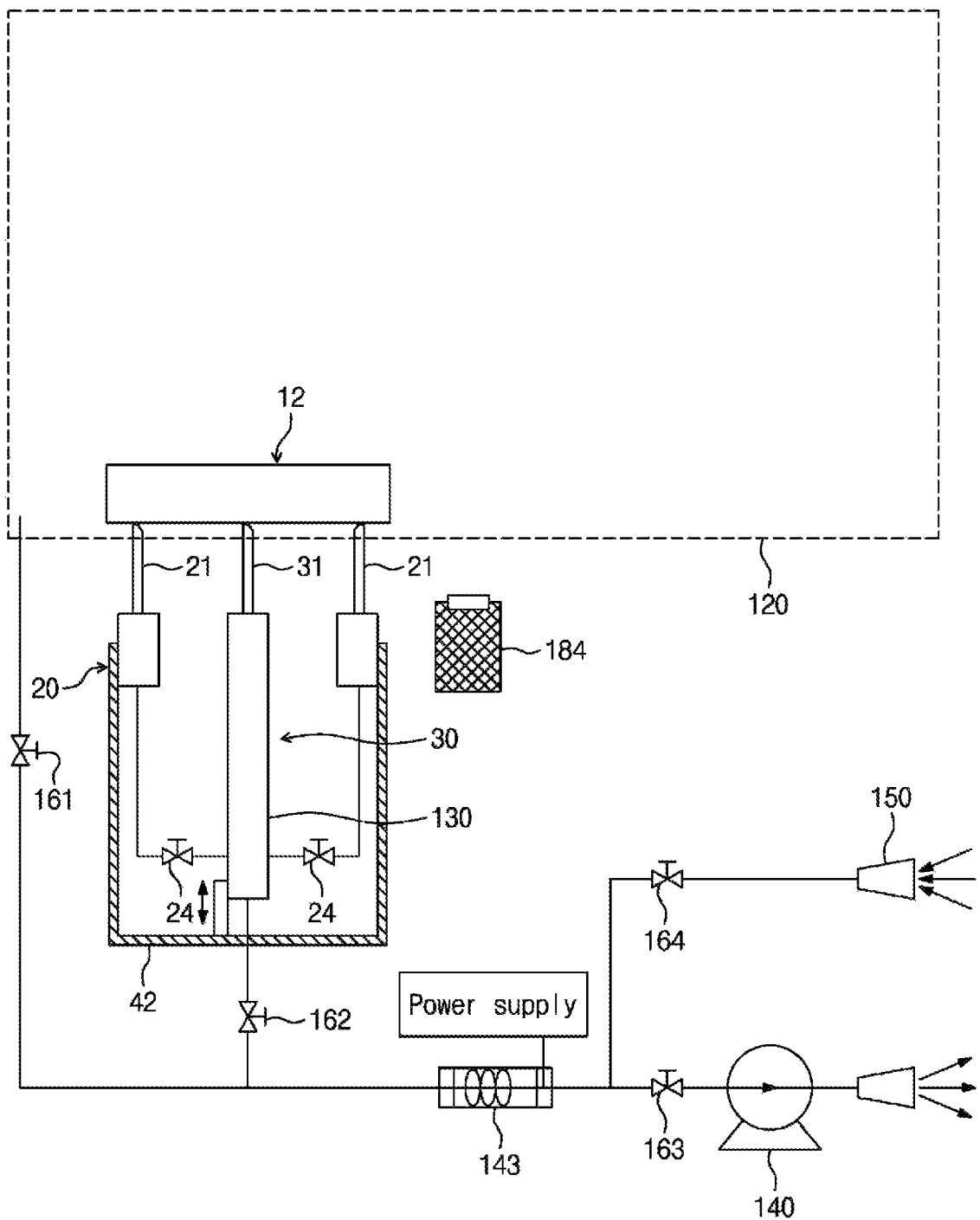
FIG. 13 is a conceptual diagram of a sterilization apparatus according to another embodiment of the present disclosure.

FIG. 13 is a conceptual diagram of a sterilization apparatus according to another embodiment of the present disclosure.

Referring to FIG. 13, the sterilization apparatus 100 includes: the sterilant extractor 20 extracting the sterilant 243 using an auxiliary needle 21 from the sterilant cartridge 12 disposed inside or outside the sterilization chamber 120; and the sterilant supplier 30 which receives the sterilant extracted through the auxiliary needle, vaporizes the sterilant through a vaporizer, and provides the vaporized sterilant to the sterilization chamber or a vacuum pouch disposed inside the sterilization chamber through a main needle. The sterilant extractor 20 and the sterilant supplier 30 are disposed outside the sterilization chamber 120. The sterilant supply valve 24 is between the auxiliary needle 21 and the sterilant supplier to adjust the sterilant extracted from the sterilant cartridge 12 to be supplied to the sterilant supplier 30. The sterilant extractor 20 and the sterilant supplier 30 may be disposed in a housing coupled to a lower surface of the sterilization chamber. The housing may include a sidewall 41 and a lower plate 42.

Only the sterilant cartridge 12 may be mounted in the sterilization chamber. In more detail, the vacuum packaging bag is removed and the sterilization space may be the sterilization chamber. Accordingly, the main needle 31 may provide a sterilant directly to the sterilization chamber 120 through the sterilant injection path stopper 251 and the sterilant injection path 250 of the sterilant cartridge. A target object may be stored directly in the sterilization chamber 120.

According to a modified embodiment of the present disclosure, the sterilant cartridge is disposed outside the sterilization chamber, and the main needle may directly supply the vaporized sterilant to the sterilization chamber.

The embodiments are examples, and thus, it will be understood by those of ordinary skill in the art that various changes in form and details may be made therein without departing from the spirit and scope of the present disclosure. Therefore, the embodiments should be considered in descriptive sense only and not for purposes of limitation.

The invention claimed is:

1. A vaporizer for vaporizing a sterilant to supply to a sterilization chamber, the vaporizer comprising:
   a sterilant injection line through which the sterilant moves to the sterilization chamber; and
   a pumping line, which is configured integrally with the sterilant injection line, through which air exhausted from the sterilization chamber moves into the vaporizer,
   wherein the pumping line has greater fluid conductance than the sterilant injection line, and
   wherein the pumping line is a pipe inserted into a vaporizer body tube.

2. The vaporizer of claim 1, wherein
   the pipe operates as a venting line that injects external air.

3. The vaporizer of claim 2, wherein the sterilant injection line is a space between the vaporizer body tube and the pipe.

4. The vaporizer of claim 3, wherein the vaporizer body tube and the pipe have a double tube structure.

5. The vaporizer of claim 1, wherein the pumping line is a pipe inserted into a vaporizer body tube, and
   an orifice or a thread is formed on an outer surface of the pipe to increase fluid resistance.

6. The vaporizer of claim 5, wherein, by forming the orifice or the thread, a residence time of the sterilant is increased and a moving speed of the sterilant is increased.

7. The vaporizer of claim 5, wherein, in an area blocked by the orifice or the thread, the sterilant is reflected to form a vortex, thereby increasing heating efficiency.

8. The vaporizer of claim 5, wherein, in order to remove impurities included in the sterilant deposited on the outer surface of the pipe, the pipe is decomposed to be replaced or cleaned.

9. The vaporizer of claim 1, wherein the sterilant injection line comprises a conductance adjuster and the sterilant moves along the conductance adjuster.

10. The vaporizer of claim 9, wherein the conductance adjuster is formed of a spiral fluid path so that a moving path of the sterilant is greater than a straight distance.

11. A sterilization device comprising:
a target object storage container storing a target object therein and receiving a sterilant;
a vacuum pump evacuating the target object storage container;
a line connecting the target object storage container to the vacuum pump; and
a main needle between the line and the target object storage container,
wherein the line comprises a sterilant injection line through which the sterilant is injected to the target object storage container, and a pumping line, which is configured integrally with the sterilant injection line, through which air exhausted from the target object storage container moves,
the pumping line has greater fluid conductance than the sterilant injection line,
the main needle inserts the sterilant into the target object storage container by puncturing a sterilant injection path stopper of the target object storage container.

12. A sterilization device comprising:
a target object storage container storing a target object therein and receiving a sterilant;
a vacuum pump evacuating the target object storage container;
a line connecting the target object storage container to the vacuum pump;
an auxiliary needle configured to puncture a sterilant cartridge and extract the sterilant stored in the sterilant cartridge; and
a sterilant supply valve,
wherein the line comprises a sterilant injection line through which the sterilant is injected to the target object storage container, and a pumping line, which is configured integrally with the sterilant injection line, through which air exhausted from the target object storage container moves,
the pumping line has greater fluid conductance than the sterilant injection line,
wherein the sterilant supply valve comprises:
an elastic pipe of elastic material disposed between the auxiliary needle and a vaporizer configured to vaporize the extracted sterilant and provide the vaporized sterilant to the sterilant injection line; and
a compressor pressing and closing the elastic pipe.

13. The sterilization device of claim 12, wherein the compressor comprises:
a pressing head configured to press the elastic pipe locally;
an elastic spring arranged to surround a lower side surface of the pressing head;
a pressing head pipe arranged to surround an upper side surface of the pressing head; and
a pressing head receiver recessed locally to receive the pressing head and fixed to the vaporizer.

\* \* \* \* \*